(12) United States Patent
Oh et al.

(10) Patent No.: US 6,968,595 B2
(45) Date of Patent: Nov. 29, 2005

(54) VACUUM CLEANER WITH ULTRAVIOLET STERILIZATION LAMP

(75) Inventors: Jang-keun Oh, Gwangju (KR); Hyun-ju Lee, Jeonju (KR)

(73) Assignee: Samsung Gwangju Electronics Co., Ltd., Gwangju (KR)

( * ) Notice: Subject to any disclaimer, the term of this patent is extended or adjusted under 35 U.S.C. 154(b) by 362 days.

(21) Appl. No.: 10/243,780

(22) Filed: Sep. 13, 2002

(65) Prior Publication Data

US 2003/0221279 A1    Dec. 4, 2003

(30) Foreign Application Priority Data

May 29, 2002  (KR) ............................... 2002-29734

(51) Int. Cl.$^7$ ............................... A47L 9/28; A47L 9/16
(52) U.S. Cl. ............................... 15/339; 15/352; 15/353; 55/DIG. 3; 55/429
(58) Field of Search ....................... 15/353, 339, 246.3, 15/350, 352; 96/224; 55/DIG. 3, 337, 429

(56) References Cited

U.S. PATENT DOCUMENTS

| | | | | |
|---|---|---|---|---|
| 2,590,152 | A | * | 3/1952 | McGowan ................... 15/339 |
| 2,632,912 | A | * | 3/1953 | Cuddeback ................... 15/339 |
| 6,428,589 | B1 | * | 8/2002 | Bair et al. ................... 15/353 |
| 6,579,334 | B2 | * | 6/2003 | Oh et al. ................... 55/DIG. 3 |
| 6,662,403 | B2 | | 12/2003 | Oh ................... 15/353 |
| 2001/0052166 | A1 | | 12/2001 | Park et al. ................... 15/353 |

FOREIGN PATENT DOCUMENTS

| | | |
|---|---|---|
| DE | 9860020 | 7/1999 |
| DE | 10157019 | 12/2002 |
| GB | 2277251 | 10/1994 |
| GB | 2368516 | 5/2002 |
| JP | 5766728 | 4/1982 |
| JP | 1151424 | 6/1989 |
| JP | 11244206 | 9/1999 |
| JP | 2001029288 | 2/2001 |
| JP | 2001346733 | 12/2001 |
| KR | 0054946 | 7/2001 |
| RU | 2153278 | 7/2000 |

* cited by examiner

*Primary Examiner*—Theresa T. Snider
(74) *Attorney, Agent, or Firm*—Ladas & Parry LLP (57) ABSTRACT

The cyclone-type dust collecting apparatus for a vacuum cleaner can reduce reverse flow of dirt and kill any bacteria in the dirt-collecting receptacle. The cyclone-type dust-collecting apparatus has a protruding flow path formed on the front side of the cyclone body and a lamp-positioning groove depressed inwardly at one side of the dirt-collecting receptacle for an ultraviolet lamp disposed in the cleaner body to apply ultraviolet rays radiated into the dirt-collecting receptacle. Accordingly, various bacteria inside the dirt collecting receptacle can be killed as the ultraviolet lamp disposed in the lamp positioning groove of the dirt collecting receptacle continuously applies the ultraviolet rays into the dirt collecting receptacle while the cleaner is on. Moreover, reverse flow of the dirt through the protruding flow path can be reduced as the storage level of the dirt stored near the protruding flow path of the dirt collecting receptacle is lowered and the space between the dirt near the protruding flow path of the dirt collecting receptacle and the cyclone body is expanded.

8 Claims, 6 Drawing Sheets

FIG.1

PRIOR ART

FIG.2

PRIOR ART

VACUUM CLEANER WITH ULTRAVIOLET STERILIZATION LAMP

BACKGROUND OF THE INVENTION

1. Field of the Invention

The present invention relates to a vacuum cleaner, and more particularly, to a cyclone-type dust-collecting apparatus separating dust and dirt from a cyclone stream by a centrifugal force formed by a cyclone stream in the suction air including dust and dirt flown in through the suction port of a vacuum cleaner.

2. Description of the Related Art

Figure 1:
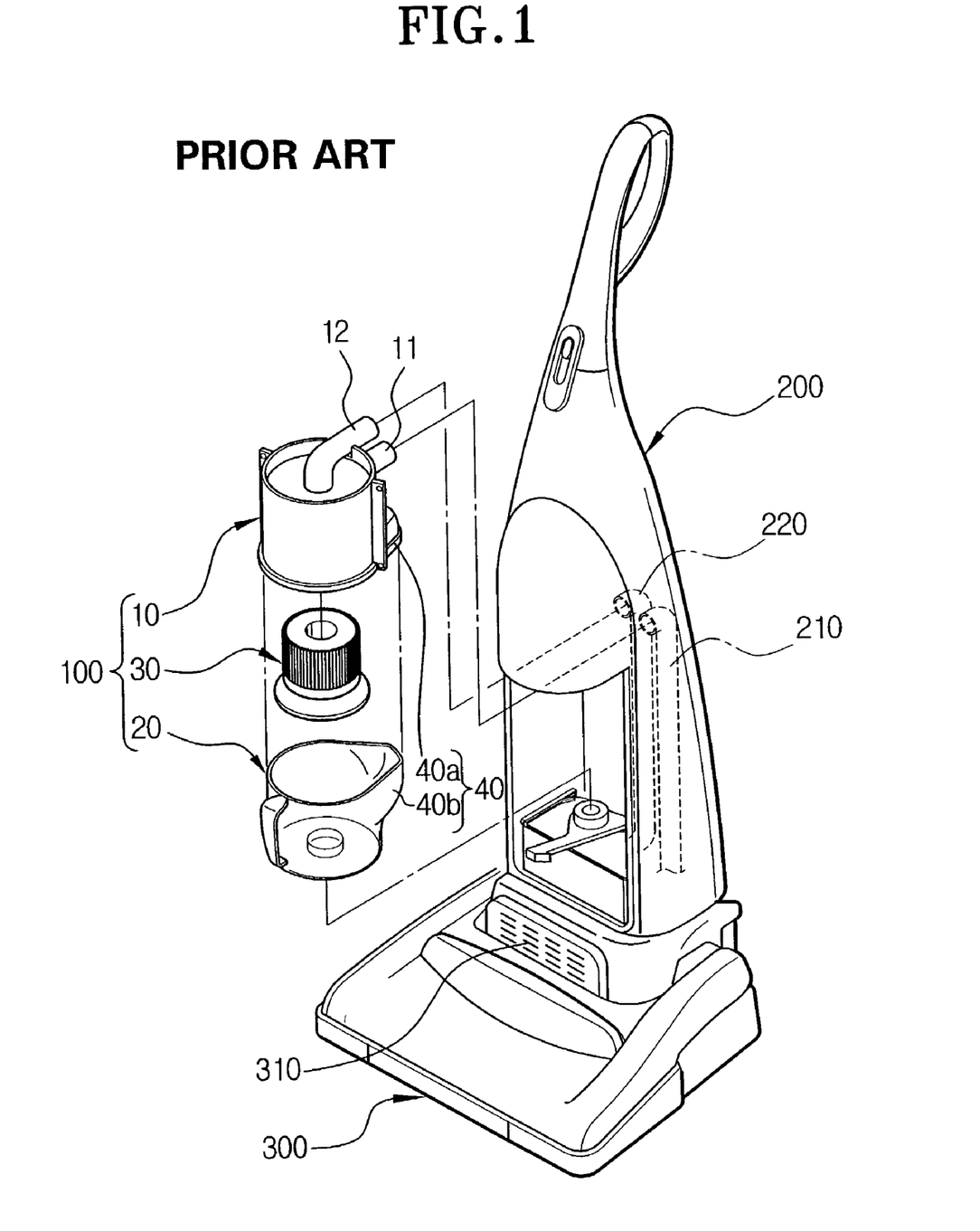
FIG. 1 is a perspective view showing a general cyclone-type dust-collecting apparatus for a vacuum cleaner.

A typical example of the above-described cyclone-type dust collecting apparatus for a vacuum cleaner is shown in FIG. 1 and described hereinafter.

In FIG. 1, the reference number 100 is a conventional cyclone-type dust collecting apparatus, 200 is a cleaner body, and 300 is a suction brush. As shown in FIG. 1, the cyclone-type dust collecting apparatus 100 has a cyclone body 10, a dirt-collecting receptacle 20, a grill assembly 30, and a protruding flow path 40.

The cyclone body 10 has an air inlet pipe 11 and an air discharge pipe 12. The air inlet pipe 11 is connected with an air inlet path 210 (shown in phantom) formed to provide a connection through a suction port (now shown) of a suction brush 300 of the cleaner body 200. The suction discharge pipe 12 is connected with an air discharge pipe 220 (shown in phantom) formed to provide a connection through a motor driving chamber 310 of the suction brush 300 of the cleaner body 200. The air, including entrained dust and dirt, flown in through the suction brush 300 passes through the air inlet path 210 and the air inlet pipe 11 and flows in direction tangential to the cyclone body 10 and accordingly a cyclone stream is formed in the cyclone body 10. The dust and dirt included in the cyclone stream is separated by centrifugal force of the circulating cyclone stream and the cleaned air is discharged outside through the air discharge pipe 12, the air discharge path 220 and the motor driving chamber 310.

The dirt collecting receptacle 20 is removably connected to the lower part of the cyclone body 10 and collects dust and dirt separated by the centrifugal force made by the cyclone stream in the cyclone body 10.

Figure 2:
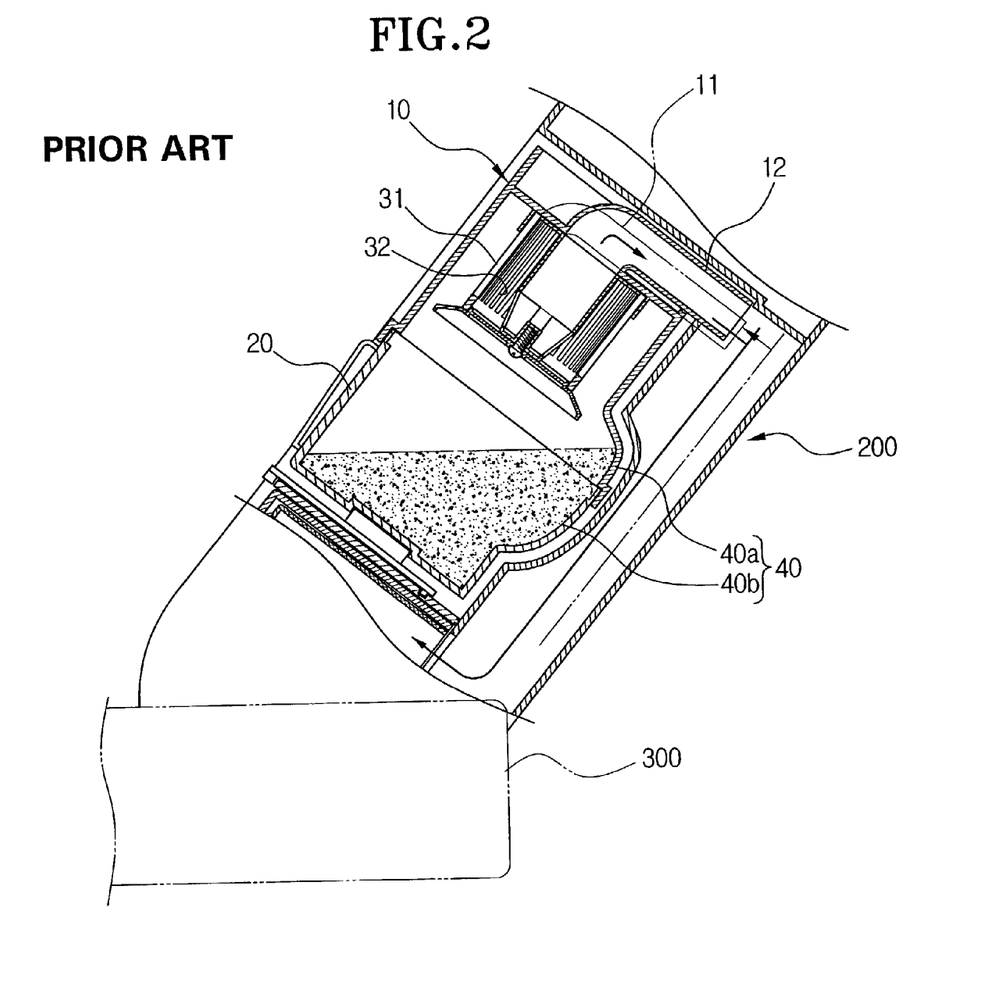
FIG. 2 is a cross-sectional view of a vacuum cleaner having a cyclone-type dust-collecting apparatus as shown in FIG. 1 during use.

The grill assembly 30, as shown in cross-section in FIG. 2, is disposed at the beginning of the air discharge path 12 inside the cyclone body 10 and prevents the dust and dirt separated from the cyclone stream from reversibly flowing through the air discharge pipe 12. The grill assembly 30 comprises a grill body 31 and a number of paths 32, disposed on the outside surface of the grill body 31, to be connected with the air discharge pipe.

The protruding flow path 40 is for large particles of dirt separated from the cyclone stream in the cyclone body 10 being smoothly collected into the dirt collecting receptacle 20 disposed below the protruding flow path 40. The protruding flow path 40 has a first protruding portion 40a and a second protruding portion 40b respectably formed by protruding one side of the lower part of the cyclone body 10 and the upper part of the dirt collecting receptacle 20 outwardly in the radial direction.

The general cyclone-type dust collecting apparatus 100 has air inlet pipe 11 and air discharge pipe 12 of the cyclone body 10 disposed at the cleaner body 200 respectively to be connected with the air inlet path 210 and the air discharge path 220 of the cleaner body 200, as shown in FIG. 2.

When the cleaner is in operation, suction force is generated in the suction brush 300 as the motor of the motor driving chamber 310 is driven. The air, including the dust and dirt found on the surface to be cleaned, is flown by the suction force in to the cyclone body 10 through the suction brush 300, the air inlet path 210 and the air inlet pipe 11. The flown in air is induced by the air inlet pipe 11 to move in an oblique or tangential direction along the inner circumference of the cyclone body 10 to form a cyclone stream and accordingly the dust and dirt included in the air are separated by the weight created by centrifugal force and is then collected in the dirt collecting receptacle 20. The cleaned air is discharged outside through the paths 32 of the grill assembly 30, the air discharge pipe 12, the air discharge path 220 and the motor driving chamber 310. During the dirt separating process, large particles of dirt are smoothly collected in the dirt-collecting receptacle 20 through the protruding flow path 40 and therefore prevent large particles of dirt flown into the cyclone body 10 from clogging the paths 32 of the grill assembly 30.

The conventional vacuum cleaner having the cyclone-type dust collecting apparatus separating the dirt from the air and collecting it by the above described structure and operation generally has the cleaner body 200 slantingly disposed to the suction brush 300 at a predetermined angle and the cyclone-type dust collecting apparatus 100 of the cleaner body 200 is also inclined in the same angle and direction that the cleaner body 200 is slanted. Therefore, the dirt stored in the dirt collecting receptacle 20 is stored at a high level on the protruding flow path 40 side of the dirt collecting receptacle 200, as shown by the dotted line in FIG. 2, and the dirt over flows through the protruding flow path 40 as the dirt level in the protruding flow path 40 side of the dirt collecting receptacle 20 reaches the level of the cyclone body 10. The dirt collected in the dirt-collecting receptacle 20 is finally discharged through the paths 32 of the grill assembly 30 and accordingly lowers cleaning efficiency and pollutes the surroundings outside the vacuum cleaner during discharge of the polluted air. Additionally, large particles of dirt unable to pass through the paths 32 may clog the paths 32, making it impossible to avoid lowering cleaning efficiency. Therefore, it is necessary to change the structure of the cleaner since reverse flow of the dirt is caused by the protruding flow path 40 disposed at the back of the cyclone body 10, i.e., on the cleaner body 200.

Meanwhile, the dirt collecting receptacle 20 for storing dirt in the vacuum cleaner having the cyclone-type dust collecting apparatus provides a suitable place for the various bacteria to live and breed. Accordingly, various bacteria, such as mites, exist in the dirt collecting receptacle 20, and it causes problems as the bacteria is discharged outside together with the dirt being reversed or released with the dirt when the dirt collecting receptacle 20 is empted, thereby and polluting the environment.

SUMMARY OF THE INVENTION

In order to solve the above described problems, the present invention has been developed to provide a cyclone-type dust collecting apparatus for a vacuum cleaner which can significantly reduce the amount of the dirt reverse flowing through the protruding flow path by expanding the dirt storage unit of the dirt-collecting receptacle, particularly the space between the stored dirt near the protruding flow path and the cyclone body.

Another object of the present invention is to provide a cyclone-type dust-collecting apparatus for a vacuum cleaner capable of disinfecting the inside of the dirt-collecting receptacle and maintaining the environment outside of the vacuum cleaner clean of bacteria and dust particles.

The cyclone-type dust-collecting apparatus for a vacuum cleaner according to the present invention for achieving the above objects comprises a cyclone body comprising an air inlet pipe connected to an air inlet path formed for connection to a suction brush of a cleaner body and an air discharge pipe connected with an air discharge path formed for connection to a motor driving chamber of a cleaner body, a cyclone body for forming a cyclone stream from the air, including entrained dust and dirt flown in through the air inlet pipe, a dirt-collecting receptacle removably disposed at the lower part of the cyclone body for collecting dust and dirt separated by centrifugal force formed by a cyclone stream of the cyclone body during cleaner operation, and a grill assembly disposed at an entrance of the air discharge pipe inside the cyclone body to prevent dust and dirt from reversibly flowing through the air discharge pipe, wherein an inwardly depressed lamp positioning groove is provided adjacent one side of the dirt collecting receptacle for positioning an ultraviolet lamp disposed in the cleaner body for disinfecting the air inside the dirt-collecting receptacle.

The cyclone-type dust-collecting apparatus for a vacuum cleaner according to the present invention for achieving another object has a protruding flow path respectably formed at one side of the cyclone body and the dirt-collecting receptacle for smoothly collecting large particles of dirt separated by centrifugal force from the cyclone stream inside the cyclone body into the dirt-collecting receptacle, wherein the protruding flow path is positioned on the front side when the side of the cleaner body in which the cyclone-type dirt-collecting apparatus is disposed is defined as the back side.

Accordingly, when using the cleaner, the ultraviolet lamp located at the lamp positioning groove of the dirt collecting receptacle continuously applies ultraviolet rays to the dirt-collecting receptacle and disinfects the inside thereof.

In addition, since the protruding flow path is formed adjacent the front side of the cyclone-type dust-collecting apparatus, the storage level of the dirt stored near the protruding flow path of the dirt-collecting receptacle is lowered and therefore the space between the dirt near the protruding flow path and the cyclone body is increased and reverse flow of the dirt through the protruding flow path is subsequently reduced.

Here, the protruding flow path comprises a first protruding portion and a second protruding portion formed by protruding one side of the lower part of the cyclone body 10 and the upper part of the dirt-collecting receptacle 20 outwardly in a radial direction. A pair of grips may be disposed on the second protruding portion.

The cyclone-type dust-collecting apparatus for a vacuum cleaner of the present invention also may have a partition fixed at the lower end of the cyclone body to be located between the cyclone body and the dirt-collecting receptacle and the partition has a passage hole on which part the protruding flow path is formed. Accordingly, reverse flow of dirt can be effectively prevented as the cyclone body and the dirt-collecting receptacle is divided by the partition.

In order to achieve an object, the inventive cyclone-type dust-collecting apparatus for a vacuum cleaner comprises a suction brush moving on a surface to be cleaned and having a motor driving chamber in which a vacuum motor is disposed, a cleaner body removably connected to the suction brush at a predetermined angle and having an air discharge path formed for connection to an air inlet path connected to the suction brush, and the motor driving chamber, a cyclone body having an air discharge pipe connected to an air inlet pipe formed for connection to the suction brush, and the air discharge path forming a cyclone stream in the air, including entrained dust and dirt flown in through the air inlet pipe, a dirt-collecting receptacle removably disposed at the lower part of the cyclone body for collecting dust and dirt separated by centrifugal force generated by a cyclone steam in the cyclone body, a grill assembly disposed at the beginning of the air discharge pipe inside the cyclone body for preventing the dust and dirt from reverse flowing through the air discharge pipe, an ultraviolet lamp disposed adjacent the dirt-collecting receptacle of the cleaner body, and a lamp positioning groove recessed inwardly adjacent one side of the dirt-collecting receptacle to enable the ultraviolet lamp to be located in the dirt-collecting receptacle when it is attached to the cleaner body so as to apply ultraviolet rays.

BRIEF DESCRIPTION OF THE DRAWINGS

The aforementioned object and characteristic of the present invention will be made more apparent by describing a preferred embodiment of the present invention with reference to the accompanying drawings, in which.

DETAILED DESCRIPTION OF THE PREFERRED EMBODIMENT

Hereinafter, a preferred embodiment of the present invention will be described in greater detail with reference to the accompanying drawings.

Figure 3:
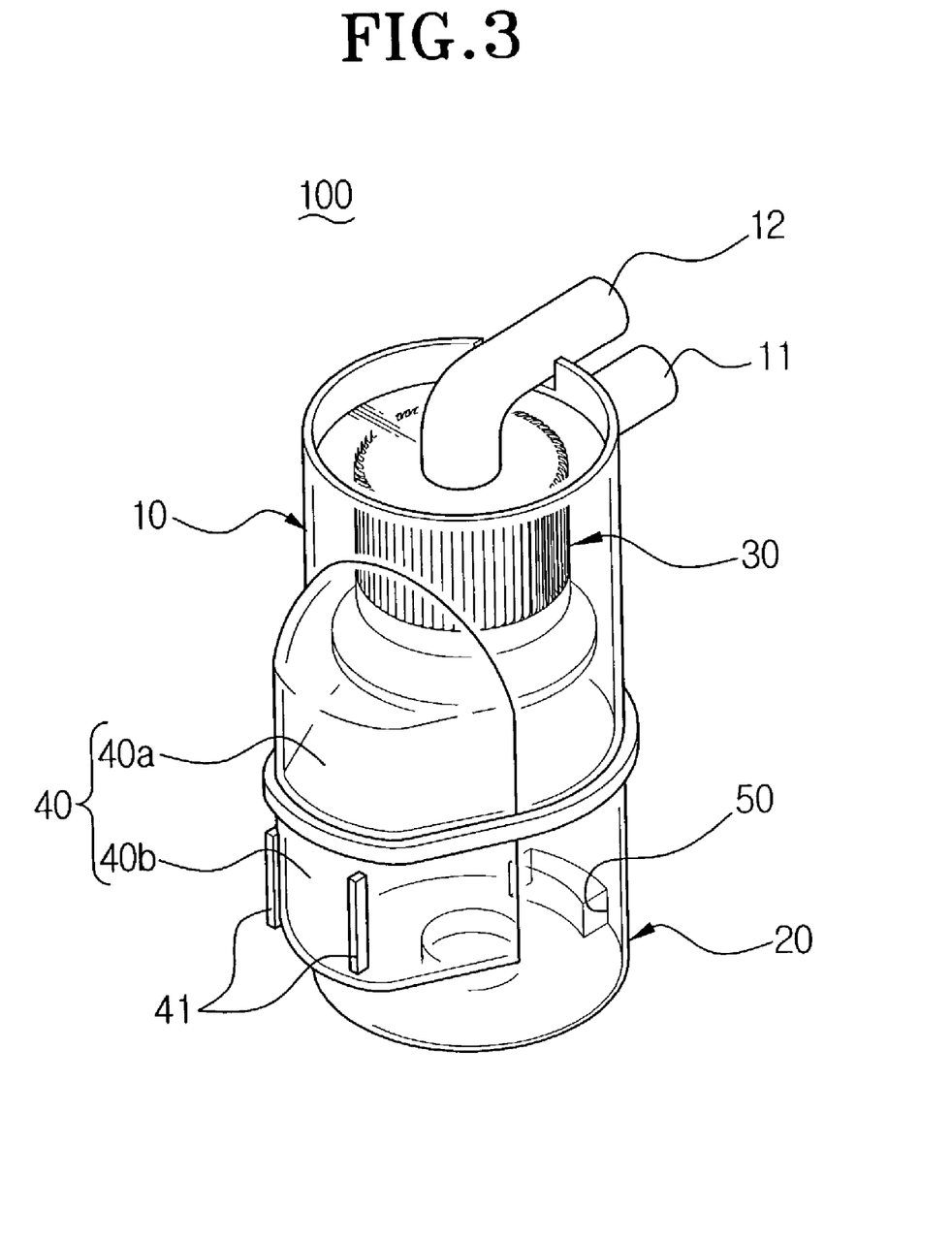
FIG. 3 is a perspective view of a cyclone-type dust collecting apparatus for a vacuum cleaner according to an embodiment of the present invention.
Figure 4:
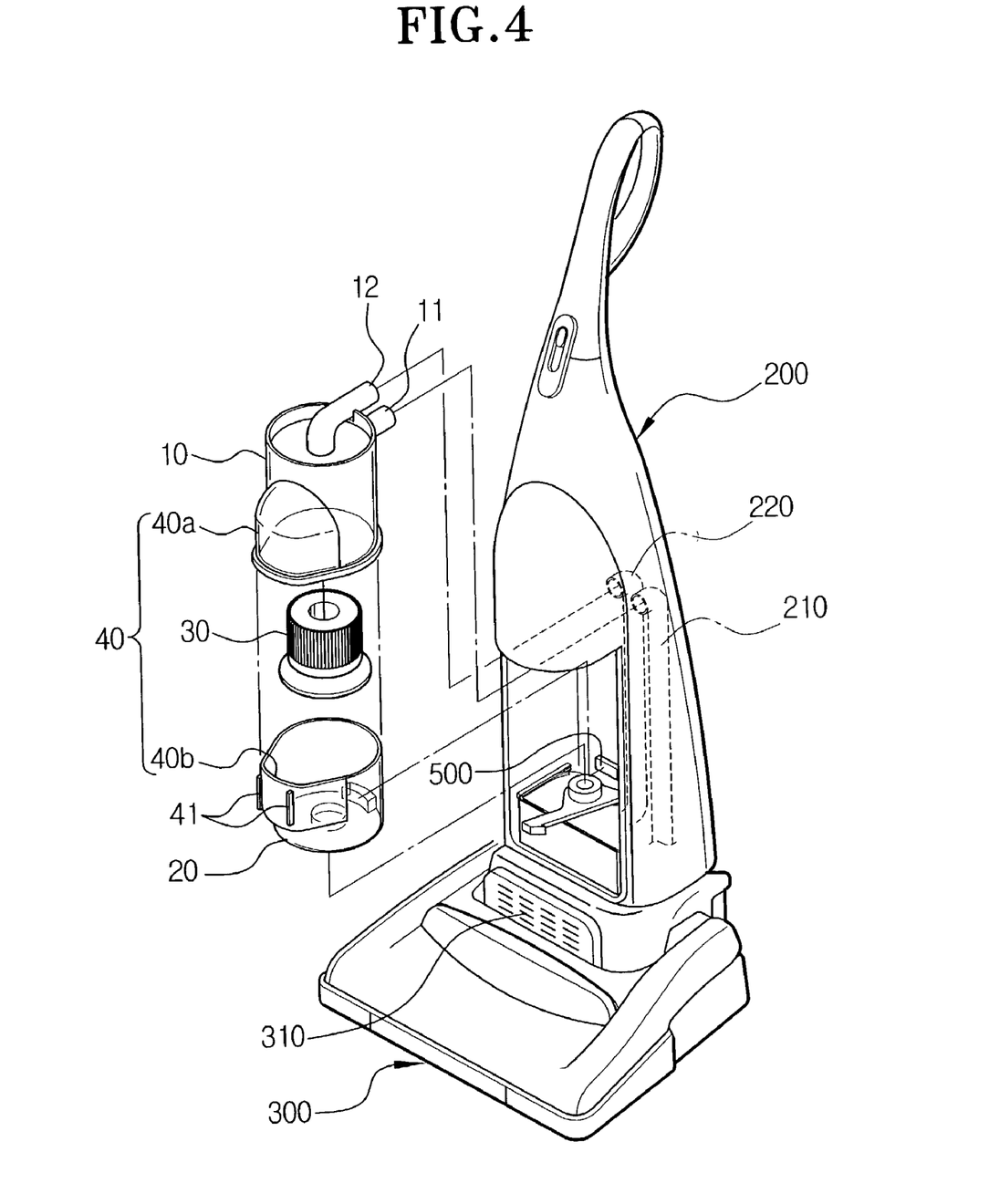
FIG. 4 is a perspective view showing a vacuum cleaner having a cyclone-type dust-collecting apparatus according to an embodiment of the present invention shown in FIG. 3.

Referring now to FIGS. 3 and 4, the cyclone-type dust collecting apparatus 100 for a vacuum cleaner according to an embodiment of the present invention comprises a cyclone body 10, a dirt-collecting receptacle 20, a grill assembly 30, a protruding flow path 40, and a lamp-positioning groove 50. As shown in FIG. 4, the vacuum cleaner comprises the cyclone-type dust collecting apparatus 100, a cleaning body 200, a vacuum brush 300, and an ultraviolet lamp 500. For purpose of the drawing figures and the description of the invention, similar elements will be indicated by identical reference numerals to those shown in FIGS. 1 and 2, above.

The cyclone body 10 has an air inlet pipe 11 and an air discharge pipe 12 and the cleaning body 200, in which the cyclone body is disposed, has an air inlet path 210 connected through with a suction port (not shown) of the suction brush 300 and an air discharge path 220 connected through with a motor driving chamber of the suction brush 300. The cyclone body 10 is disposed on the cleaner body 200 with the air inlet pipe 11 connected to the air inlet path 210 (shown in phantom in FIG. 4) and the air discharge pipe 12 connected to the air discharge path 220 (shown in phantom in FIG. 4). Accordingly, the air, including the dust and dirt flown in through the suction brush 300 during the cleaning, flows into the cyclone body 10 through the air inlet path 210 and the air inlet pipe 11 in the tangential direction and a cyclone stream is formed in the cyclone 10 thereby. The dust and dirt included in the cyclone stream is separated by centrifugal force and the cleaned air is discharged through the air discharge pipe 12, the air discharge path 220, and the motor driving chamber 310.

The dirt collecting receptacle 20 is removably connected at the lower part of the cyclone body 10 and collects the dust and dirt separated by the centrifugal force made by the cyclone stream of the cyclone body 10.

The grill assembly 30 is disposed at the beginning of the air discharge pipe 12 inside the cyclone body 10 and prevents the dust and dirt separated from the cyclone stream from reversing direction and exiting through the air discharge pipe 12. The grill assembly 30 comprises a grill body 31 and a number of paths 32 disposed on the outside surface of the grill body 31 to be connected through with the air discharge pipe 12.

The protruding flow path 40 is for smoothly collecting large particles of dirt separated from the cyclone stream of the cyclone body 10 into the dirt collecting receptacle 20 below and comprises a first and a second protruding portions 40a, 40b, respectively, formed by protruding one side of the lower part of the cyclone body 10 and the upper part of the dirt collecting receptacle 20 outwardly in the radial direction.

Figure 5:
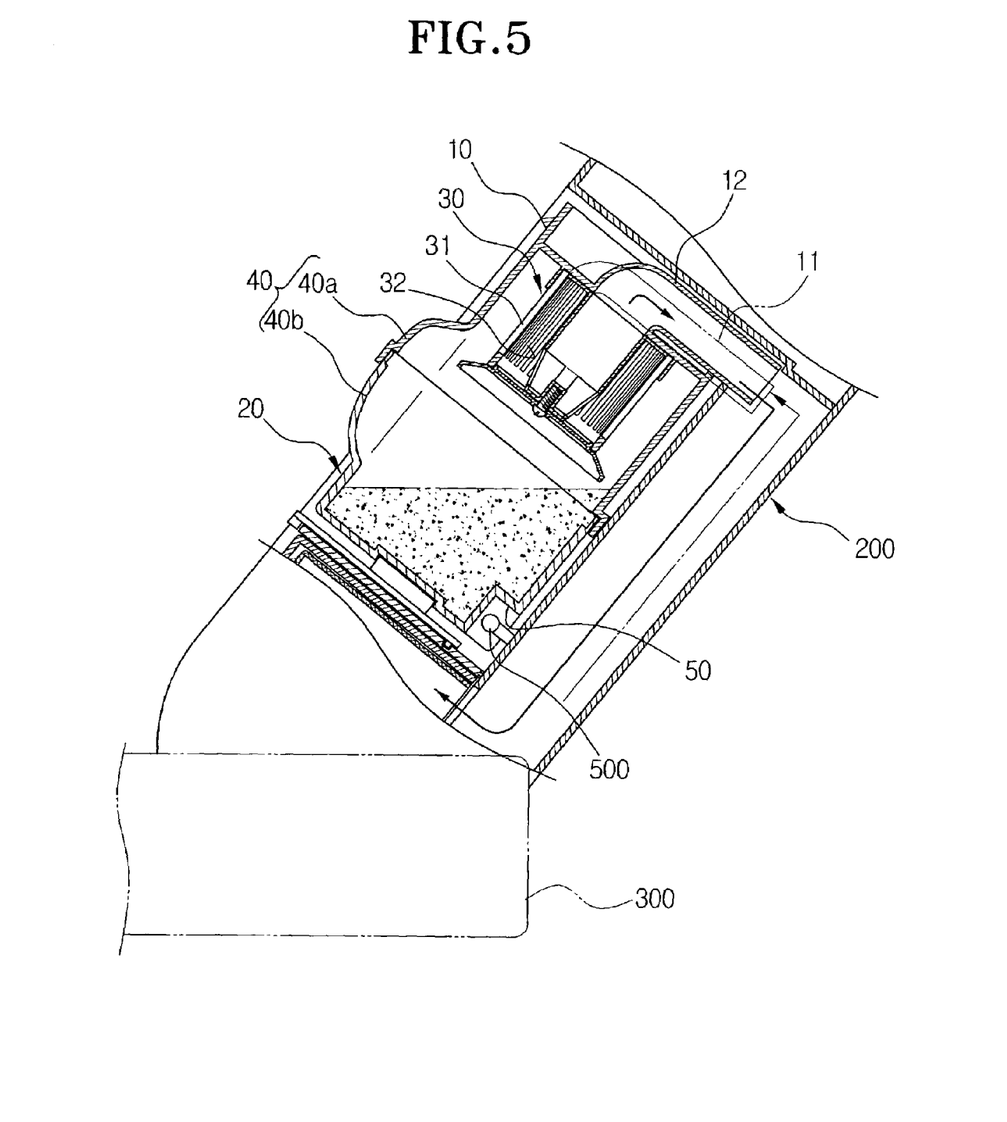
FIG. 5 is a cross-sectional view showing a vacuum cleaner shown in FIG. 4 during use.

The structure and shape of the protruding flow path 40 is not significantly different from the conventional one but the characteristic of the protruding flow path of the cyclone-type dust collecting apparatus according to the present invention is that, unlike the conventional one, the protruding flow path is located on the front side when the side the cyclone dust collecting apparatus is disposed on the cleaner body 200 is considered to be on the back side, as is more clearly shown in FIG. 5. Accordingly, it is beneficial that, when the vacuum cleaner is in use, the storage level of the dirt stored in the dirt collecting receptacle 20, particularly the storage level of the dirt near the protruding flow path 40 of the dirt collecting receptacle 20, is at a lower position, as shown in dashed line in the drawing during the process of separating and collecting dirt while the cyclone-type dust collecting apparatus being slanted in the predetermined angle that the cleaner body 200 is slanted. Therefore, the space between the dirt near the protruding flow path 40 of the dirt collecting receptacle 20 and the cyclone body 10 is expanded and reverse flow of the dirt through the protruding flow path 40 can be significantly reduced compared to that of a conventional one. Meanwhile, the second protruding portion 40b formed on the side of the dirt collecting receptacle 20 may have at least a pair of grips 41 for gripping so as to enable a user to easily remove the dirt collecting receptacle 20 from the cleaner body 200 or the cyclone body 10 by using the grips 41 provided.

The lamp positioning groove 50 is formed at the lower bottom of the back side of dirt collecting receptacle 20 to be recessed inwardly to a predetermined depth and the ultraviolet lamp 500 is disposed at one side of position where the cyclone-type dust collecting apparatus of the cleaning body 200 is disposed. When the dirt-collecting receptacle 20 is disposed in the cleaner body 200, the ultraviolet lamp 500 (FIGS. 4 and 5) is received within and is positioned in the lamp-positioning groove 50. The ultraviolet lamp 500 is switched on when the vacuum cleaner is driven and therefore will continuously apply ultraviolet rays generated by the ultraviolet lamp 500 to the inside of the dirt collecting receptacle 20 while the vacuum cleaner is in use. As a result, various bacteria in the dirt-collecting receptacle 20 can be killed by the ultraviolet rays and therefore reduce the number of bacteria inside the dirt collecting receptacle 20 that can be discharged and/or released outside the vacuum cleaner. That is to say, the cleanliness of the environment can be maintained.

Figure 6:
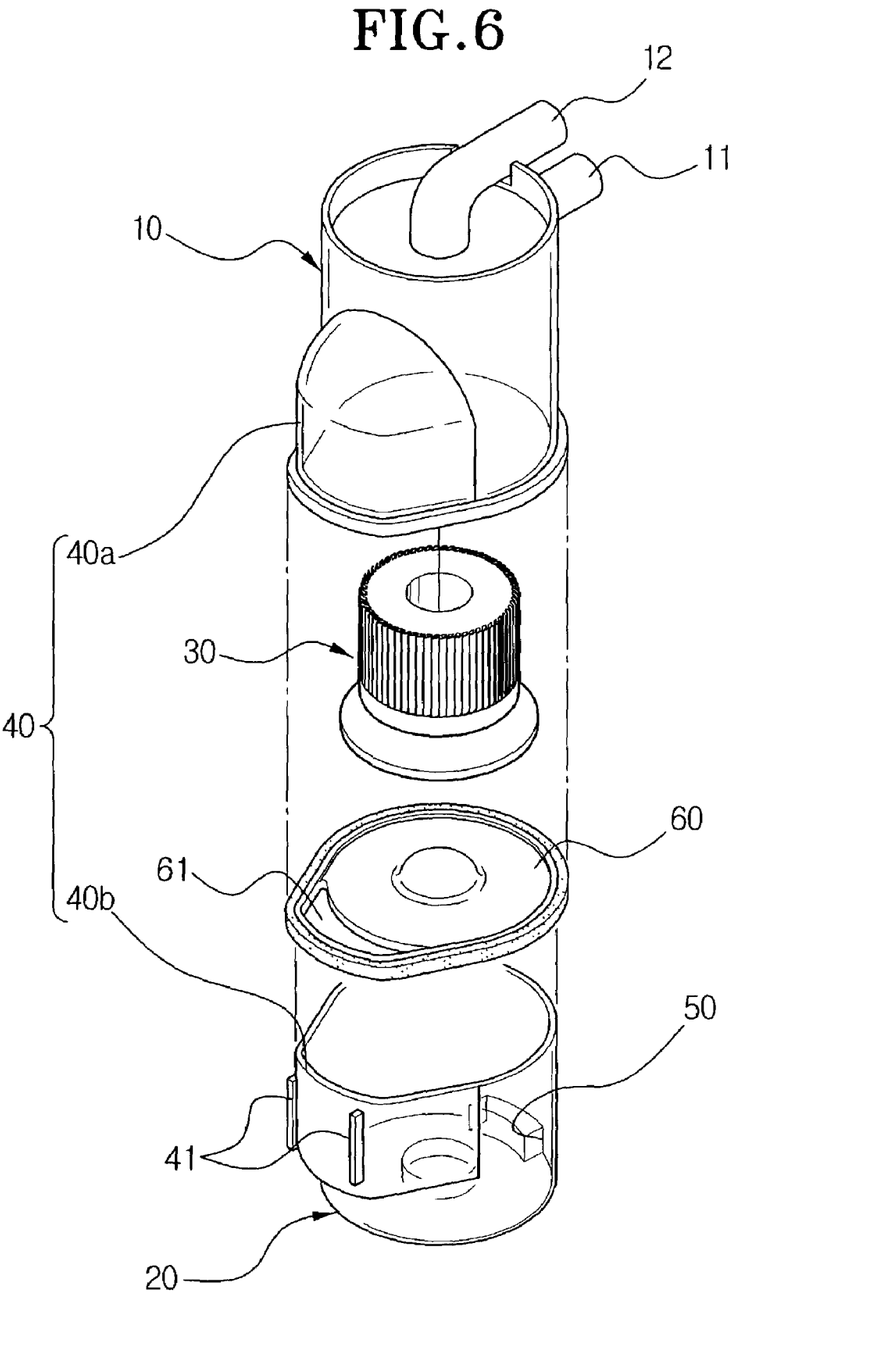
FIG. 6 is a perspective view showing a cyclone-type dust-collecting apparatus according to another embodiment of the present invention.

Meanwhile, according to another embodiment of the present invention, as shown in FIG. 6, the cyclone-type dust collecting apparatus has a partition fixed at the lower end of the cyclone body 10 to be located in between the cyclone body 10 and the dirt-collecting receptacle 20. The partition 60 has a passage hole 61 formed on the part in which the protruding flow path is formed and the dirt separated from the air in the cyclone body 10 can be collected into the dir-collecting receptacle 20 through the passage hole 61. However, the dirt collected in the dirt-collecting receptacle 20 can hardly flow back to the cyclone body 10 as the dirt-collecting receptacle 20 and the cyclone body 10 is divided by the partition 60. In other words, the partition 60 can effectively prevent reverse flow of the dirt toward the grill assembly 30. Since the structure, is except the partition 60 is identical to the pre-described embodiment, a detailed description will be omitted by simply giving the identical reference numbers of the structure to like elements.

FIG. 5 in a cross-sectional view schematically shows the vacuum cleaner having the cyclone-type dust collecting apparatus according to the present invention, as described above, during use.

As shown, the cyclone-type dust collecting apparatus 100 has an air inlet pipe 11 connected with an air inlet path 210 (not shown in FIG. 5) of the cleaner body 200 and an air discharge pipe 12 through with an air discharge path 220 (not shown in FIG. 5) both disposed within the cleaner body 200. The dirt-collecting receptacle 20 is connected with the cyclone body 10. Additionally, the ultraviolet lamp 500 provided with the cleaner body 200 is positioned in the lamp positioning groove 50 of the dirt collecting receptacle 20 as the cyclone-type dust collecting apparatus 100 is disposed in the cleaner body 200.

When the cleaner is in operation, suction force is generated by the suction brush 300 as the motor of the motor driving chamber 310 is driven. The air, including the dust and dirt from the surface to be cleaned, is flown into the cyclone body 10 by the suction force and through the suction brush 300, the air inlet path 210 and the air inlet pipe 11. The flown-in air is induced to move in an oblique or tangential direction along the inner circumference of the cyclone body 10 to form a cyclone stream by the air inlet pipe 11 and accordingly the dust and dirt included in the air are separated by centrifugal force and collected in the dirt-collecting receptacle 20. The cleaned air is discharged outside through the paths 32 of the grill assembly 30, the air discharge pipe 12, the air discharge path 220 and the motor driving chamber 310. The above dirt separating process is not very different from the conventional process.

However, since the protruding flow path 40 of the present invention being a discharge path for large particles of dirt is formed on the front side of the cyclone-type dust collecting apparatus 200, the storage level of the dirt stored near the protruding flow path 40 of the dirt collecting receptacle 20 is lowered and the space between the dirt and the cyclone body 10 is expanded as shown in the dashed line in the drawing indicating the dirt level and therefore reverse flow of the dirt through the protruding flow path can be dramatically reduced.

Furthermore, according to the present invention, ultraviolet rays generated by the ultraviolet lamp 500 located in the lamp positioning groove 50 of the dirt collecting receptacle 20 are continuously applied to the inside of the dirt collecting receptacle 20 while the vacuum cleaner is in use and therefore bacteria in the dirt collecting receptacle 20 is eliminated. That is, the environment will not be polluted by bacteria as no bacteria can live inside the dirt-collecting receptacle 20.

According to the present invention described above, since the protruding flow path is formed in front side of the cyclone-type dust-collecting apparatus, when the vacuum cleaner is in use, the space between the dirt collected and stored in the dirt-collecting receptacle and the cyclone body can be expanded and therefore reverse flow of the dirt through the protruding flow path can be significantly reduced. Hence, the conventional problem of the environment being polluted and the paths of the grill assembly being clogged, caused by the large amount of dirt reversed through the protruding flow path, can be resolved.

Moreover, according to the present invention, the bacteria inside the dirt-collecting receptacle can be eliminated as the ultraviolet rays are continuously applied to the dirt-collecting receptacle during operation of the vacuum cleaner and therefore pollution due to the bacteria can be prevented.

Although the preferred embodiments of the present invention have been described, it will be understood by those skilled in the art that the present invention should not be limited to the described preferred embodiments. Various changes and modifications can be made within the sprit and scope of the present invention as defined by the appended claims.

What is claimed is:

1. A cyclone-type dust-collecting apparatus for a vacuum cleaner comprising:
    a cyclone body comprising an air inlet pipe connected to an air inlet path formed for connection to a suction brush of a vacuum cleaner body and an air discharge pipe connected with an air discharge path formed for connection to a motor driving chamber of a vacuum cleaner body, the cyclone body for forming a cyclone stream from air, including entrained dust and dirt flown in through the air inlet pipe, said cyclone body further comprising a protruding flow path formed on one side of the cyclone body and a dirt collecting receptacle, said protruding flow path collecting large particles of dirt and dust separated from a cyclone stream inside the cyclone body by centrifugal force, said protruding flow path being positioned on the front side of the cyclone body wherein the side of the dust-collecting apparatus disposed on the cleaner body is considered to be the back side;
    the dirt collecting receptacle removably disposed at the lower part of the cyclone body for collecting dust and dirt separated by centrifugal force formed by the cyclone stream of the cyclone body during vacuum cleaner operation; and
    a grill assembly disposed at an entrance of the air discharge pipe inside the cyclone body to prevent dust and dirt from reversibly flowing through the air discharge pipe,
    an ultraviolet lamp disposed in the vacuum cleaner body, said ultraviolet lamp emitting ultraviolet light into the dirt collecting receptacle;
    wherein a lamp positioning groove depressed inwardly in the dirt collecting receptacle is provided for positioning the ultraviolet lamp disposed in the vacuum cleaner body, said ultraviolet lamp for disinfecting air inside the dirt collecting receptacle.

2. The cyclone-type dust collecting apparatus for a vacuum cleaner as in claim 1, wherein the protruding flow path comprises a first protruding portion and a second protruding portion formed by protruding one side of the lower part of the cyclone body and an upper part of the dirt collecting receptacle outwardly in a radial direction.

3. The cyclone-type dust collecting apparatus for a vacuum cleaner as in as claim 2, wherein the second protruding portion has at least a pair of grips.

4. The cyclone-type dust collecting apparatus for a vacuum cleaner as in claim 1, wherein a partition is provided between the cyclone body and the dirt collecting receptacle so as to be fixed at the lower part of the cyclone body and the partition has a passage hole corresponding to the protruding flow path.

5. A cyclone-type vacuum cleaner comprising:
    a suction brush for cleaning a surface and having a motor driving chamber in which a vacuum motor is disposed;
    a cleaner body removably connected to the suction brush at a predetermined angle and having an air inlet path and an air discharge path, said air inlet path connected through with a suction port of the suction brush, said air discharge path connected through with a motor driving chamber of the suction brush;
    a cyclone body having an air inlet pipe connected to the air inlet path of the cleaner body and having an air discharge pipe connected to the air discharge path of the cleaner body, said cyclone body forming a cyclone stream of air, including dust and dirt in flown through the air inlet pipe, said cyclone body further comprises a protruding flow path formed on the front side of the cyclone body, wherein the side of the cyclone body facing the cleaner body is the back side of the cyclone body;
    a dirt-collecting receptacle removably disposed at the lower part of the cyclone body for collecting dust and dirt separated by centrifugal force made by a cyclone steam in the cyclone body;
    a grill assembly disposed at the beginning of the air discharge pipe inside the cyclone body for preventing dust and dirt from reverse flowing through the air discharge pipe;
    an ultraviolet lamp disposed adjacent the dirt-collecting receptacle of the cleaner body; and
    a lamp-positioning groove recessed inwardly in the dirt-collecting receptacle to enable the ultraviolet lamp to be located adjacent the dirt-collecting receptacle when the dirt-collecting receptacle is attached to the cleaner body so as to enable the ultraviolet lamp to apply ultraviolet rays into the dirt-collecting receptacle.

6. The cyclone-type vacuum cleaner as in claim 5, wherein the protruding flow path comprises a first protruding portion and a second protruding portion respectively formed by protruding one side of the lower part of the cyclone body and an upper part of the dirt collecting receptacle outwardly in the radial direction.

7. The cyclone-type vacuum cleaner as in claim 6, wherein the second protruding portion has at least a pair of grips.

8. A cyclone-type dust collecting apparatus for a vacuum cleaner as in claim 5, comprising a partition located between the cyclone body and the dirt-collecting receptacle wherein the partition has a passage hole on the part in which the protruding flow path is formed.

* * * * *